United States Patent
Ge et al.

(10) Patent No.: US 12,230,371 B2
(45) Date of Patent: Feb. 18, 2025

(54) METHOD AND SYSTEM FOR GENERATING AN INPUT FOR A SEARCH ENGINE

(71) Applicant: KONINKLIJKE PHILIPS N.V., Eindhoven (NL)

(72) Inventors: Xin Ge, Shanghai (CN); Jin Sheng, Shanghai (CN)

(73) Assignee: Koninklijke Philips N.V., Eindohoven (NL)

( * ) Notice: Subject to any disclaimer, the term of this patent is extended or adjusted under 35 U.S.C. 154(b) by 190 days.

(21) Appl. No.: 17/777,448

(22) PCT Filed: Nov. 17, 2020

(86) PCT No.: PCT/EP2020/082315
§ 371 (c)(1),
(2) Date: May 17, 2022

(87) PCT Pub. No.: WO2021/099283
PCT Pub. Date: May 27, 2021

(65) Prior Publication Data
US 2023/0360749 A1    Nov. 9, 2023

(30) Foreign Application Priority Data

Nov. 18, 2019 (WO) ............... PCT/CN2019/119127
Dec. 30, 2019 (EP) ................................. 19219964.4

(51) Int. Cl.
*G16H 10/60* (2018.01)
*G06F 16/9532* (2019.01)

(52) U.S. Cl.
CPC ......... *G16H 10/60* (2018.01); *G06F 16/9532* (2019.01)

(58) Field of Classification Search
None
See application file for complete search history.

(56) References Cited

U.S. PATENT DOCUMENTS

| | | |
|---|---|---|
| 5,715,449 A | 2/1998 | Peters |
| 6,801,916 B2 | 10/2004 | Roberge |
| 8,375,014 B1 | 2/2013 | Brocato |
| 8,388,530 B2 | 3/2013 | Shusterman |
| 2004/0153343 A1* | 8/2004 | Gotlib ............... G16H 10/60 705/3 |

(Continued)

OTHER PUBLICATIONS

Amri et al. ("ECG signal processing using offline-wavelet transform method based on ECG-IoT device," 2016 3rd International Conference on Information Technology, Computer, and Electrical Engineering (ICITACEE), Semarang, Indonesia, 2016, pp. 1-6) (Year: 2016).*

(Continued)

*Primary Examiner* — Christopher B Tokarczyk

(57) ABSTRACT

An input mechanism for generating an input for a search engine, which is of particular use in searching medical databases comprising electrocardiogram (ECG) results. The input for the search engine is constructed in iterative stages, by initializing the input with a placeholder symbol, and iteratively replacing (responsive to a user input) placeholder symbols with input sections. An input section may comprise a variable to be searched, one or more additional placeholder symbols or a function.

14 Claims, 9 Drawing Sheets

(56) References Cited

U.S. PATENT DOCUMENTS

| | | | |
|---|---|---|---|
| 2007/0156677 A1 | 7/2007 | Szabo | |
| 2010/0161646 A1* | 6/2010 | Ceballos | G06F 16/2428 |
| | | | 707/769 |
| 2013/0091170 A1 | 4/2013 | Zhang | |
| 2013/0132117 A1* | 5/2013 | Barsoum | G16H 30/20 |
| | | | 705/3 |
| 2013/0151572 A1* | 6/2013 | Brocato | G06F 16/2428 |
| | | | 707/805 |
| 2014/0082013 A1* | 3/2014 | Wolf | G06F 16/245 |
| | | | 707/769 |
| 2014/0172864 A1* | 6/2014 | Shum | G16H 10/60 |
| | | | 707/740 |

OTHER PUBLICATIONS

Kokkinaki, A. et al., Searching biosignal databases by content and context: Research Oriented Integration System for ECG Signals (ROISES). Computer Methods and Programs in Biomedicine (2011).
International Search Report for PCT/EP2020/082315 filed Nov. 17, 2020.

* cited by examiner

METHOD AND SYSTEM FOR GENERATING AN INPUT FOR A SEARCH ENGINE

CROSS-REFERENCE TO PRIOR APPLICATIONS

This application claims the priority benefit under 35 U.S.C. § 371 of International Patent Application No. PCT/EP2020/082315, filed on Nov. 17, 2020, which claims the priority benefit of International Patent Application No. PCT/CN2019/119127, filed on Nov. 18, 2019 and European Patent Application No. 19219964.4, filed on Dec. 30, 2019, the contents of which are herein incorporated by reference.

FIELD OF THE INVENTION

The present invention relates to the field of search engines, and in particular to concepts for generating an input for a search engine.

BACKGROUND OF THE INVENTION

There is an ongoing and increasing desire for improving the ease and accuracy with which a user is able to search a database, such as those that store electrocardiography (ECG) information of one or more patients. In such databases, there are one or more entries of ECG information. Each entry of ECG information typically comprises at least one (raw) ECG waveform (obtained from one or more sensors monitoring the patient) and one or more parameters derived from the waveform(s) or otherwise associated with the patient (e.g. waveform measurements, diagnoses and/or patient demographic information).

Increasing an ease and accuracy of searching is particularly important in the field of clinical research, in which it is desirable to perform complex search queries. In particular, there is a strong desire to increase an ease of searching for an ECG waveform, as these are particularly complex, which makes it difficult to accurately prepare a specific query for the database.

However, it is recognized that searching for an ECG waveform is particularly difficult. This at least partly stems from the fact that an ECG waveform is a continuous signal, and is typically stored in a separate database or file to its associated one or more parameters (where the files are linked with pointers or similar methods) or encoded into a Base64 (or similar) format in the same database as the other ECG information. The (continuous signal) nature of the ECG waveform, and the standard storing mechanism for ECG waveforms makes it difficult to search directly for elements of the waveform.

Typically, these problems are at least partly overcome by indirectly searching for a portion of the waveform by searching based on other ECG information (and identifying the portion of the waveform associated with the searched ECG information). There is therefore an ongoing need for decreasing the complexity of searching an ECG waveform.

Typical search engines permit a user to manually provide an input for a search, e.g. using a keyboard, such as manually inserting desired topics, values or other criteria. The search engine may then process this input to search a database for relevant results, i.e. results that are match or are similar to the criteria identified in the input. Depending upon the search engine and the database, the results may include one or more documents, files, records, links, pointers and so on. The search engine presents the results of the search to the user.

In the context of searching ECG information, a user may be able to provide an input for searching for specific parameters of the ECG waveform and/or other characteristics of the ECG waveform or patient. The search engine identifies entries of ECG information (comprising at least the ECG waveform) that meet the search criteria, and returns these entries to the user.

However, manually inputting a search can be troublesome, especially for an inexperienced user of the search engine or if a user wishes to perform a search for results that meet some complex criteria.

US2004/0153343A1 disclose a query system, configured to access or obtain patient data from a medical information system comprising a set of electronic devices including means for monitoring patients, wherein said query system comprises: A. a query script generator for defining one or more query scripts, each of said query scripts comprising a set of query attributes associated with elements of a subset of patient data; a query script executor, configured to apply said query script to said patient data and to generate query results comprising said elements of said subset of patient data; and an out generator, configured to output said query results. The query system further includes a query wizard graphical user interface, which facilitate the display, defining and filtering specific attributes so as to enable a user to obtain search results as desired with support of the query wizard. However, the query system does not allow a user to compose a query as an input for search engine intuitively.

There is therefore a desire for a new mechanism for enabling user input for a search engine. In particular, there is a desire for a new mechanism that ensures potentially complex criteria for a search can be input quickly, simply and effectively by a user, with reduced error.

SUMMARY OF THE INVENTION

The invention is defined by the claims.

According to examples in accordance with an aspect of the invention, there is provided a computer-implemented method of generating an input for a search engine.

The method comprises: initializing a visual representation of an input for the search engine, the initialized visual representation of the input comprising at least one interactive placeholder symbol; displaying the visual representation of the input using an interactive visual display system; iteratively performing a replacement process until the visual representation of the input no longer comprises any placeholder symbols, the replacement process comprising steps of: in response to a user interacting with a placeholder symbol, displaying one or more input sections, for interaction with by the user, using the visual display system; and in response to a user interacting with a displayed input section, replacing the placeholder symbol with the displayed input section; and generating the input for the search engine using the visual representation of the input, wherein each of the one or more input sections comprises at least one of: an interactive placeholder symbol, a variable for an input for the search engine and/or a value for a variable.

The invention proposes the use of placeholders within an interactive, visual representation of an input for a search engine, such as those designed for searching an electrocardiogram (ECG) database, in order to enable a user to intuitively and readily prepare the input, by appropriately replacing the placeholders with elements for the input. This allows the user to intuitively build-up an entire visual representation of the input, which can then be processed by the search engine.

The present invention initializes a visual representation by populating a visual representation with one or more placeholders. The placeholders can then be replaced by the user with one or more input sections (e.g. potential portions for an input), to thereby allow the user to build up the desired input.

An input section can be preset (or follow a fixed format) to avoid the user providing an input section that is unallowable or does not meet the search tool criteria, e.g. an incorrectly formatted date. The placeholders of the initialized input may be replaced with further placeholders (e.g. a single placeholder of the initialized input may be replaced by an input section having multiple placeholders). This allows the user to increase the complexity and detail of the input.

The present invention therefore provides a new user interface or mechanism that enables a user to provide an input in an intuitive manner, and reduces the likelihood that the user will enter an undesired or unallowable input value (e.g. miss a parenthesis or function).

A placeholder is an icon or symbol that represents a potential portion of an input for a search engine. An interaction may include, for example, a user operating a mouse, keyboard or other user input device to select a displayed placeholder or other element displayed by the visual display system.

Of course, if there is only a single placeholder symbol, which is replaced by a variable or a value for an input to the search engine, then only a single iteration of replacing the placeholder symbol may take place.

The search engine is preferably designed for searching a database storing one or more entries of electrocardiography, ECG, information of one or more patients. Electrocardiography information comprises any information of an ECG waveform or derived therefrom. Thus, in some examples, each entry of ECG information in the ECG database comprises at least one ECG waveform and/or information derived from an ECG waveform, such as characteristics of a particular ECG waveform (i.e. "electrocardiogram features" or "ECG features"). An entry of ECG information may comprise, for example, a diagnosis result (indicating a diagnosis of the patient, e.g. as derived from the ECG waveform) and/or a diagnosis statement (which is a code identifying a diagnosis of the patient, e.g. as derived from the ECG waveform). An entry of ECG information may further comprise other characteristics of the patient (e.g. patient identifying data or patient demographic data).

In such embodiments, the variables and/or values are of the one or more input sections are designed for searching an entries of a database storing ECG information. In particular, they enable variables or parameters of ECG information to be identified in order to identify ECG waveforms associated with said parameters. Put another way, the variables and/or values may be designed for enabling the search of ECG information, e.g. variables may relate to parameters of an ECG waveform, parameters derived from an ECG waveform and/or parameters of the patient (e.g. demographic information such as "age" or "gender").

For example, the variable for the input for the search engine may comprise an identifier of a parameter for searching an entry of electrocardiogram information, such as a characteristics of an ECG waveform (e.g. maximum, minimum or average values of an ECG waveform) and/or identifying data of the ECG waveform (such as an identifying number associated with a set of one or more waveforms).

In some embodiments, each entry of the database comprises at least one ECG waveform of a patient and one or more of: a value for a parameter derived from the ECG waveform and a value for a parameter of the patient associated with the at least one ECG waveform. Correspondingly, the variable for the input for the search engine may comprise an identifier of a parameter derivable from at least one ECG waveform of a patient or a parameter of the patient associated with the at least one ECG waveform.

It is noted that a parameter comprises any category of information. A value for a parameter may be numerical, descriptive (e.g. a text parameter, such as a diagnosis statement) and/or categorical. Examples of parameters derived from the ECG waveform include an ECG feature (e.g. maximum), a diagnosis result, a diagnosis statement and so on. Examples of parameter of the patient include any parameter of demographic or historical information of the patient, such as an age of the patient, a gender of the patient, a patient history, electronic medical record information and so on.

Put more generally, in some embodiments, each entry of the database comprises at least one ECG waveform of a patient and one or more of: information derived from the ECG waveform and information of the patient associated with the at least one ECG waveform; and the variable for the input for the search engine comprises an identifier of an element of information derivable from at least one ECG waveform of a patient or an element of information of the patient associated with the at least one ECG waveform.

In embodiments, at least one of the one or more input sections comprises one or more interactive placeholder symbols.

In some embodiments, each input section that comprises one or more interactive placeholder symbols comprises an input section comprising at least one function and at least one interactive placeholder symbol.

This embodiment provides a method for inserting a function into an input. A function may, for example, indicate a relationship (e.g. AND, "OR", "+", or "max") between at least two variables, or between a variable and a value. Other functions may indicate a relationship between a variable and a desired search (e.g. "−" or "NOT" may indicate an instruction to not search for a certain variable). This improves a level of detail that the user is able to provide to an input, and provides a novel mechanism for including functions within an input.

Optionally, at least one input section comprises at least one function and at least two interactive placeholder symbols.

The step of initializing a visual representation of an input for the search engine may comprise: displaying at least two interest topics, for selection by the user, using the visual display system; in response to a user selecting one or more of the interest topics, displaying one or more possible visual representations of an input, for selection by the user, using the visual display system, each displayed possible visual representation of an input being dependent upon the one or more interest topics selected by the user; and in response to a user selecting a possible visual representation of an input, initializing the visual representation of the input based on the selected possible visual representation of the input.

The step of generating the input for the search engine may comprise generating a query script for searching a database using the visual representation of the input. In other embodiments, the visual representation of the input it provided as the input to the search engine (e.g. the characters and symbols forming the visual representation).

Optionally, the step of display one or more input sections comprises: displaying a first menu icon and a second menu icon to the user, using the visual display system; in response to the user interacting with the first menu icon, displaying a first set of one or more input sections to the user, using the visual display system, each input section in the first set comprising one or more variables and/or values for an input for a search engine; and in response to the user interacting with the second menu icon, displaying a second set of one or more input sections to the user, using the visual display system, each input section in the second set comprising one or more selectable placeholder symbols.

To increase an ease in selecting between variables, values and selectable placeholder symbols, the corresponding input sections may be listed under different headings. This increases an ease with which a user can access their desired input sections.

Of course, there may be further sub-menu icons displayed upon a user interacting with the first/second menu icon, with which the user may need to interact in order for the one or more input sections to be displayed.

In some embodiments, the step of displaying one or more input sections during the replacement process comprises: displaying at least two interest topics, for selection by the user, using the visual display system; and in response to a user selecting one or more of the at least two interest topics, displaying one or more input sections, for interaction with by the user, using the visual display system, wherein the displayed one or more input sections are dependent upon the one or more interest topics selected by the user.

This embodiment restricts the input sections that are displayed to the user to those most relevant to their desired interest topic area(s), thereby improving an efficiency of generating the input. This helps guide the user to their desired input sections, and thereby increases an ease in generating the input for the search engine.

The computer-implemented method may further comprise performing a search using the generated input for the search engine.

According to examples in accordance with an aspect of the invention, there is provided a computer program comprising code means for implementing any previously described method when said program is run on a processing system.

According to examples in accordance with an aspect of the invention, there is provided a processing system adapted to generate an input for a search engine. The processing system is adapted to: initialize a visual representation of an input for the search engine, the initialized visual representation of the input comprising at least one interactive placeholder symbol; display the visual representation of the input using an interactive visual display system; iteratively perform a replacement process until the visual representation of the input no longer comprises any placeholder symbols, the replacement process comprising steps of: in response to a user interacting with a placeholder symbol, displaying one or more input sections, for interaction with by the user, using the visual display system; and in response to a user interacting with a displayed input section, replacing the placeholder symbol with the displayed input section; and generate the input for the search engine using the visual representation of the input, wherein each of the one or more input sections comprises at least one of: an interactive placeholder symbol, a variable for an input for a search engine and/or a value for a variable.

Preferably, the at least one of the one or more input sections comprises one or more selectable placeholder symbols.

In embodiments, each input section comprises one or more interactive placeholder symbols comprises at least one function and at least one interactive placeholder symbol.

Optionally, at least one input section comprises at least one function and at least two interactive placeholder symbols.

According to examples in accordance with an aspect of the invention, there is provided an input interface system comprising: any herein described processing system; and an interactive visual display adapted to enable a user to interact with elements displayed by the visual display. The interactive visual display may comprise a display and one or more user input devices (such as a mouse, keyboard or the like).

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
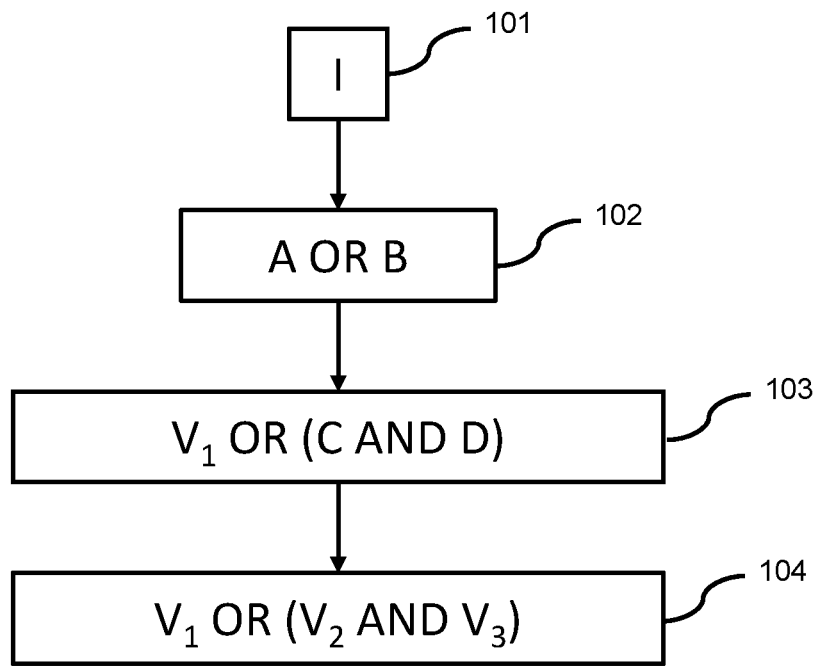
FIG. 1 conceptually illustrates the generation of an input for a search engine.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a new input mechanism for generating an input for a search engine for medical databases comprising electrocardiogram (ECG) information or results. The input for the search engine is constructed in iterative stages, by initializing the input with a placeholder symbol, and iteratively replacing (responsive to a user input) placeholder symbols with input sections. An input section may comprise a variable to be searched, a value to be searched, one or more additional placeholder symbols and/or a function.

Embodiments are based on the realization that preparation of a complex input for a search engine is difficult for an inexperienced user, as they are unused to the syntax or language used to prepare the input. However, it has been recognized that if a user is able to construct the input in stages, then errors will be reduced, leading to improved ease of preparing the input. A new input mechanism is thereby provided.

Embodiments may be employed in researching clinical databases, for example, for clinicians to identify historic results, outcomes of patients, perform statistical analysis and/or machine learning. This is of particular use in researching or investigating electrocardiogram (ECG) results or information, as such databases are complex and often required specific and precise search values. In particular, embodiments may be employed in search toolsets for searching an ECG-based database.

The invention will be described in the context of generating an input for a search engine adapted to search a database comprising one or more entries of electrocardiogram information. An entry of electrocardiogram information may comprise one or more electrocardiogram (ECG) waveforms of a patient and one or more of: a parameter derived from the waveform(s) or a parameter otherwise associated with the patient. This may include patient demographic information and/or diagnosis information of the patient.

The proposed concepts are particularly advantageous in such embodiments, as (due to the complex nature of such databases) preparing an input for a search engine of such a database is a difficult and time-consuming task, and may require knowledge of query language beyond the remit of a clinician or researcher. Indeed, one of the most important features of an ECG research toolset is flexible search.

By way of example, consider a scenario in which a clinician wishes to investigate Left Ventricular Hypertrophy (LVH). In this scenario, the clinician may wish to search data based on one or more of following example inputs:

SV1+RV5>35

(RI−SI)+(SIII−RIII)>16

SIII+max(*R/S*) any lead >30

(RaVL+SV3)*QRSduration>2436

(Max(*R/S*)precordial lead)AND(statement=LAD)

Normally, ECG waveforms for diagnosis comprise a waveform obtained from each of at least 12 leads, including 6 limb leads (I, II, III, aVL, aVR, aVF), and 6 precordial leads (V1-V6).

For the sake of completeness, it is noted that the acronyms, features and variables used in the above examples of suitable inputs are well known in the field of electrocardiography. For example, LAD refers to "Left Axis Deviation" and RaVL refers to the voltage of the R wave amplitude obtained from an aVL(augmented Vector Left) lead acquisition. The other acronyms are well known in the art.

In the first example input, SV1 is the S wave amplitude in lead V1, and RV5 is the R wave amplitude in lead V5. These are all ECG magnitude measurements in millimeters. A diagnosis of LVH (Left Ventricular Hypotrophy) may be given when the sum of the two measurements is bigger than 35 mm (i.e. the first example input is a search for a diagnosis of LVH).

In the second example input, RI and RIII refers to R wave amplitude in leads I and III respectively, while SI and SIII are S wave amplitude in leads I and III respectively.

In the third example input, "max(R/S) any lead" means the maximum value of any of any of the leads: RI/SI, RII/SII, RIII/SIII . . . RV6/SV6. Effectively, this input means to calculate the ratio of 2 measurements in all 12 leads and then identify the maximum calculated ratio.

In the fourth example input, RaVL means the R wave amplitude in lead aVL, and SV3 is S wave amplitude in lead V3. QRS duration is the time duration of QRS wave, normally it is calculated using all 12 leads (e.g. to reduce noise or error).

In the fifth example input, Max(R/S) precordial lead means Max(RV1/SV1, RV2/SV2, RV3/SV3, RV4/SV4, RV5/SV5, RV6/SV6). "statement=LAD exist" means that LAD(left axis deviation) diagnosis has been obtained based on the ECG waveform, e.g. automatically by an algorithm or by manually physician, which is included in the ECG information accompanying the ECG waveform.

As can be seen, the input criteria can be complex, and difficult to accurately enter into a search engine manually (e.g. due to syntactic complexities). There is therefore a desire to assist the clinician in defining the search input simply and effectively, so that it can be easily integrating into a search user interface.

Generally speaking, an input for a search engine can be divided into "variables", "values", and "functions".

A variable is an identifier or label of a parameter or element of electrocardiogram information that can be searched (e.g. "average heart rate", "RR interval", "LAD", "Diagnosis" or "RaVL"). The term "parameter" is considered to be effectively interchangeable with the term "variable". Here, the parameter of electrocardiogram information may comprise either a parameter derivable from an ECG waveform (e.g. "average heart rate", "RR interval", "LAD" or "RaVL"), a parameter of the patient associated with the ECG waveform (e.g. "Diagnosis Code", "Age" or "Gender") and/or an identifying parameter for an entry of the ECG database (e.g. an identifying number).

A value identifies a value for a variable (e.g. "16", "30", "Arrhythmia" or "exists"). The value for a variable may depend upon the nature of a variable.

A function (e.g. an expression) may identify either a relationship or process to be performed on between two variables or values, or between a variable and a value, (e.g. "OR", "MAX", "+", "−", or ">") or a logical process to be performed on a value of a variable (e.g. "NOT"). Thus, if an input for a search engine is formatted as "((X=A) AND B) OR (NOT(C))", this is formatted from one variable (X), three values (A, B and C) and four functions ("=", "AND", "OR" and "NOT").

The skilled person would appreciate how a variable could be implicit within a search input. For example, in a scenario in which a user wishes to search for patients diagnosed with arrhythmia, they may simply provide an input "Arrhythmia" (which here acts as a value), rather than needing to provide an input "Diagnosis=Arrhythmia" (formed of a variable—"Diagnosis"; a function "=" and a value "Arrhythmia". It is therefore not essential that all possible elements of an input are provided.

Alternatively, a value may be implicit within a search input. For example, in the scenario in which a user wishes to search for patient diagnosed with "Arrhythmia", the term "Arrhythmia" may be considered a variable (e.g. having at least possible values of "Present" or "Not Present"). A user providing an input of only "Arrhythmia" may imply that they are looking for cases having "Arrhythmia=Present".

An input provided to a search engine thereby only requires, at a minimum, at least one variable and/or at least one value.

FIG. 1 conceptually illustrates the generation of an input for a search engine for a database storing one or more entries of ECG information, following a process according to an embodiment of the invention.

Conceptually, the invention relies on a concept of building up an input for a search engine (i.e. a search query) for searching an ECG database by iteratively replacing placeholder symbols with input sections. This iterative process is performed until there are no placeholder symbols left. An input section may define a variable/value for the search query or provide additional placeholder symbols to be replaced. An input section may comprise a function for defining a desired search criteria with respect to a variable/value. The iterative process allows the input to be built up in various stages, thereby allowing a complex search query to be constructed in stages. This approach leads to reduced errors in preparing the search query, and in particular leads to a reduced chance of syntactic errors.

Initially, a visual representation of an initialized input 101 is presented to a user (via a user interface).

The initialized input comprises a placeholder symbol "I". The placeholder symbol is designed to be interactive, so that a user can replace the placeholder symbol with an input section by interacting with visual representation of the initialized input on the user interface, appropriate examples of which will be described later. An input section may comprise, for example, one or more other placeholder symbols and/or one or more variables and/or one or more functions for forming the input to the search engine.

In the illustrated example, the placeholder "I" of the initialized input is replaced by a first input section, thereby forming a first iteration of the input 102. The exemplary first input section here comprises two placeholder symbols "A" and "B" and a function "OR". The function "OR" here defines a relationship between the two placeholder symbols for the search.

As would be understood by the skilled person, the function "OR" within an input would specifically indicate that a search is performed to identify elements containing any one or more of the input sections defined within the function "OR".

The input 101, 102 is iteratively processed in this manner until the input no longer comprises any placeholder symbols.

For the sake of clarity, an input that does not comprise any placeholder symbols may be referred to as a "final input" and an input that has been modified from the initialized input, but still comprises at least one placeholder symbol, may be referred to as an "intermediate input".

In the illustrated example, as the first iteration of the input 102 comprises two placeholder symbols, i.e. it is still an intermediate input and not yet a final input, then the placeholders need to be replaced by further input sections.

In the illustrated example, the placeholder "A" of the first iteration of the input 102 is replaced by a second, different input section and the placeholder "B" of the first iteration is replaced by a third, different input section. This forms a second iteration of the input 103. The second input section here comprises a variable $V_1$ that replaces the placeholder "A". The third input section here comprises another two placeholder symbols "C" and "D" and a function "AND" (linking the placeholder symbols C and D). The function "AND" again defines a relationship between the two placeholder symbols for the search (i.e. that both "C" and "D" need to be included as features in any search result).

By way of example, the variable $V_1$, in the context of providing an input for a search engine of an ECG database, may comprise a variable "LAD", LAD indicates a "left axis deviation", a well-known term in electrocardiography.

The second iteration of the input 103 still contains at least one placeholder symbol, i.e. is still an intermediate input and not yet a final input. There is therefore a need for at least one further iteration to replace the placeholder symbol(s) with input sections.

In the illustrated example, the placeholder "C" is replaced by a fourth input section and the placeholder "D" is replaced by a fifth input section. The fourth input section here comprises another variable "V2" and the fifth input section comprises another variable "V3". This creates a third iteration of the input 104.

The third iteration of the input 104 does not comprise any placeholder symbols, meaning that a final input has been formed. The iterative replacement process therefore ends.

The conceptual diagram shown in FIG. 1 thereby illustrates how an initialized input can be iteratively processed to generate a more complex input for the search engine. This is performed by iteratively replacing any remaining placeholder symbols with an input section, responsive to a selection of the user.

In the above example, values are implicit in the final input.

The diagram of FIG. 1 also provides a number of examples of suitable replacement input sections for a placeholder symbol. In particular, a replacement input section may comprise one or more variables/values (e.g. a desired feature or value to be searched), one or more placeholder symbols (e.g. to create more complex search queries) and/or one or more functions (e.g. to create relationships between different variables/values or to create a range for a value of a variable within a search).

One of the possible input sections may indicate that a value is desired for the input. The value may be numerical or categorical. The magnitude of a numerical value may be defined by the user (e.g. typing in the magnitude). Thus, selecting a value to replace the placeholder symbol may comprise replacing the placeholder symbol with a default value (e.g. 0), and enabling the user to edit the default value to results in a desired value (e.g. 100).

A function may be a "simple function" which provides either a relationship between or process to be performed on two variables/values or a logical process to be performed on a variable/value (e.g. "A OR B", or "NOT"). A function may alternatively be a "complex function" which indicates a relationship between more than two variables (e.g. AND(A, B, C)).

Of course, any of the illustrated variables, placeholders or functions (in FIG. 1) may be replaced by combinations of one or more variables, one or more values, one or more placeholder symbols and/or one or more functions. In other words, an input section comprises a combination of one or more variables, one or more values and/or one or more placeholder symbols and/or one or more functions.

There is the potential for an input section to be reasonably complex (e.g. comprise multiple variables, multiple values and/or multiple functions). By way of example, an input section may comprise any of the example inputs previously described (e.g. "SV1+RV5>35"— which is formed of two variables SV1, RV5, one value 35 and two functions "+" and ">").

Using a functional example, the variable $V_1$ may instead be a simple equation which defines a plurality of variables and functions. By way of example, for preparing an input for searching an ECG database, the variable $V_1$ may be represented by the equation "((RaVL+SV3)*QRSduration>2436)". This illustrates how an input section may be potentially complex, allowing a user to select a complex input without needing to manually insert it.

The content of the input sections may be predetermined, for example, based on common historical searches or known desirable searches in the prior art. The content of the input sections may be controlled by an operator of the search engine or provider of the proposed mechanism for providing the input, for example.

In some embodiments, the content of the input sections presented to a user is dependent upon the content of other inputs sections already selected by a user. For example, selection of certain inputs sections may filter for certain input sections to replace remaining placeholders in the input. As another example, a content of a possible value (acting as an input section) may depend upon the variables and/or functions in the vicinity of the placeholder symbol to be replaced (e.g. to only provide values that are associated with the variable).

In some embodiments, a selected input section (that replaces a placeholder symbol) may made be interactive, so that a user can replace the input section with a different input section. This allows a user to correct any errors (e.g. if they accidentally select a wrong input section), to change their mind or to edit a selected input section (e.g. edit a magnitude of a value). This may also enable a user to amend a complex input section (e.g. which could itself be formed of more than one different input section) to more precisely define the input for the search engine.

The "final" input, being the iteration of the input generated when there are no placeholder symbols left, represents an input suitable for being processed by a search engine. It is possible for this final input to be processed so that it can act as an input for a search engine.

However, it is also possible for an input for a search engine to be generated based on more than one initialized input (i.e. from multiple final inputs). For the sake of distinction, the input used to operate the search engine is referred to as the "overall input". The overall input can therefore be generated based on only a single initialized input, or based on multiple initialized inputs, as hereafter described. Each "final input" (generated from a respective initialized input) may therefore be an element of an overall input for the search engine.

In particular, generation of an overall input for a search engine based on multiple initialized inputs can be achieved by enabling the user to define the number of initialized inputs that are used to generate the input for the search engine. Selection of the number of initialized inputs could be achieved by providing an interactive icon for creating a new initialized input or a slider for selecting a number of initialized inputs to be provided.

Each initialized input is then processed in the manner previously described, to create respective final inputs. The input for the search engine is created when each (of the at least one) input no longer comprises any placeholder symbols, i.e. only final inputs remain.

It is therefore possible that more than one initialized/intermediate/final input may be visually represented on a display at any given time.

Of course, it will be clear one or more further initialized inputs may be added at any time, such as the iterative process for replacing placeholder symbols of the original initialized input or after all displayed inputs no longer comprise any placeholder symbols.

When all displayed initialized inputs have been processed, so that there are no longer any placeholder symbols left, (and no further initialized inputs are desired), this forms the overall input that can be processed to act as an input for a search engine. Thus, all displayed inputs may be combined in order to generate the search query for the search engine. The method of combining the displayed inputs, i.e. the logic used to combine the final inputs to form the overall input (e.g. AND or OR logic) may be defined by the user.

Thus, multiple inputs, not comprising any placeholder symbols, may be combined to create the overall input that operates the search engine. The logic combination of the multiple inputs (e.g. whether AND or OR logic is used) may be defined by the user. In some embodiments, the overall input (whether created from a single or multiple initialized input(s)) is converted into a database search script to perform a search of the database. Methods of converting an input (string) into a database search script are well established in the prior art. The database search script may be formatted, for example, in the Xquery XML format or SQL format.

Embodiments may comprise searching a database using the overall input and/or a script generated from the overall input. Methods of searching a database based on an input are well known in the prior art.

Embodiments may therefore comprise performing a search using the generated/overall input for the search engine. Generating the generated input for the search engine may comprise generating a query script for searching a database using the visual representation of the (overall) input.

Performing the search may return one or more entries of electrocardiogram information (of course, no results are returned if no appropriate electrocardiogram information is identified). Each returned entry would include at least one ECG waveform of a particular patient, as previously described, and/or one or more parameters (and their values) derived from the ECG waveform and/or otherwise associated with the patient. A user may be able to select or decide the content of a returned entry (e.g. whether only the ECG waveform(s) is/are returned or whether ECG waveform(s) and parameters derived from the ECG waveform(s) are returned, e.g. by selecting which parameters are to be returned). This may be controlled using the user interface.

Figure 2:
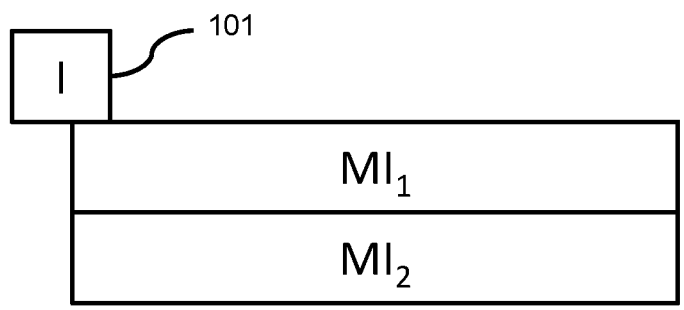
FIG. 2 illustrates a visual representation of an input following a first user interaction.
Figure 3:
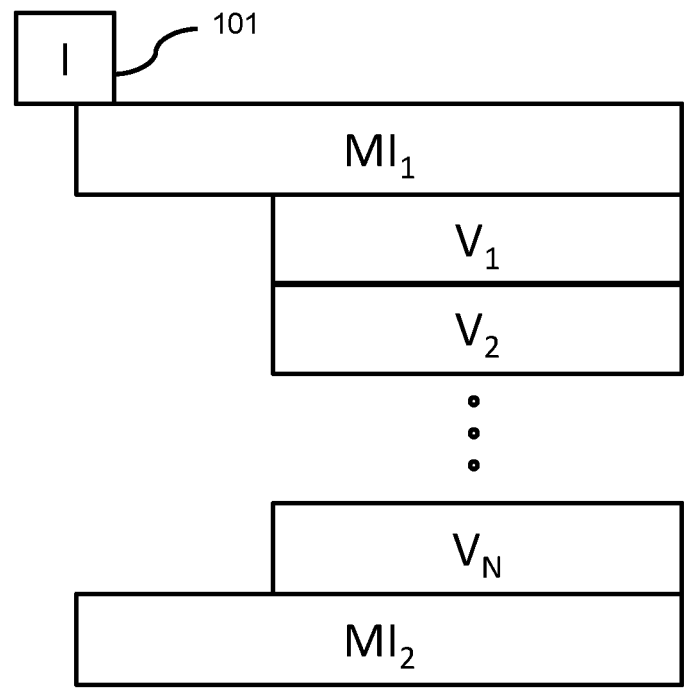
FIG. 3 illustrates a visual representation of an input following a second user interaction.
Figure 4:
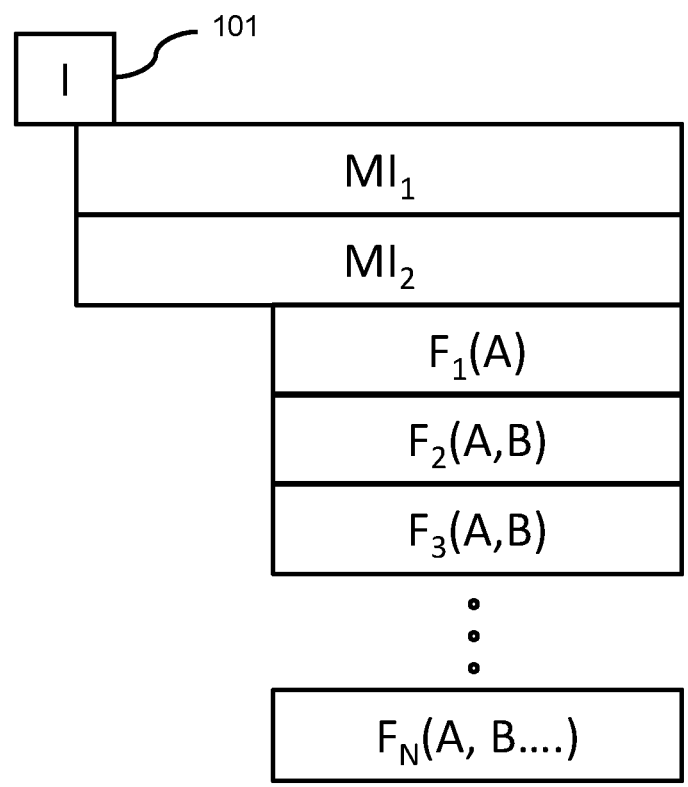
FIG. 4 illustrates a visual representation of an input following a third user interaction.

FIGS. 2 to 4 illustrate a method for replacing a placeholder symbol with an input section. This is provided in the context of replacing the placeholder symbol I in the initialized input 101 with an input section, but may be adapted for replacing any placeholder symbol.

In these figures, a menu-based system is provided within drop-down boxes from the interactive placeholder symbol. However, the menu-based system may be provided in a different window or portion of a display, as would be understood by the skilled person.

FIG. 2 illustrates a possible display provided in response to the user interacting with a placeholder symbol "I".

In response to the user interacting with the placeholder symbol "I" (of the initialized input 101), a menu 210 is displayed. The menu 210 here comprises a first menu icon 211 and a second menu icon 212. Both menu icons 211, 212 are interactive.

FIG. 3 illustrates a possible display provided in response to the user interacting with the first menu icon 211.

In response to the user interacting with the first menu icon 211, a first set of one or more input sections is displayed to the user. Each one or more input sections here comprises one or more variables $V_1$-$V_N$ for an input for the search engine. The user is able to select or interact with one of these input sections. The selected input section replaces the placeholder symbol.

The precise variables made available for selection by a user will depend upon the available parameters or variables stored by entries in the ECG database. Thus, the format of the entries in the ECG database may define or control the variables made available for selection by a user.

Selecting the first menu icon 211 thereby enables a user to select with which variable the placeholder symbol is to be replaced.

FIG. 4 illustrates a possible display provided in response to the user interacting with the second menu icon 212.

In response to the user interacting with the second menu icon, a second set of one or more input sections may be displayed to the user. Each of the input sections in the second set comprise one or more selectable placeholder symbols A, B, and optionally one or more functions $F_1$, $F_2$, $F_3$ ... $F_N$. As before, the user is able to select or interact with one of these input sections. The selected input section replaces the placeholder symbol.

Thus, selecting the second menu icon 211 enables a user to select with which variable the placeholder symbol is to be replaced.

The proposed menu-based system effectively enables a user to be able to build up a more complex query by replacing the placeholder with different placeholders and/or functions.

Of course, another menu icon may trigger the display of input sections corresponding to different values. Another example of a menu icon may be a menu icon that replaces the placeholder symbol with a default, editable value.

Indeed, these examples of menus are non-exhaustive, and are intended to illustrate the flexibility of the system in enabling different input sections to be presented to the user for selection.

For example, in some embodiments, selecting a menu icon will cause additional sub-menu icons to be displayed (which may operate in a similar manner to any previously described menu item).

For example, selecting a first sub-menu icon may cause yet further sub-menu icons to be displayed ("sub-sub-menu icons"), whereas selecting a second sub-menu icon may cause input sections to be displayed. It will be appreciated that yet further sub-menus could be presented in response to selecting a sub-menu icon.

It will therefore be clear that interacting with the placeholder symbol may initiate a menu-based protocol for displaying (or controlling the display of) one or more input sections for selection by a user.

Different menus or sub-menus may enable different input sections or combinations of input sections to be displayed. For example, one (sub-)menu (displayed when a certain (sub-)menu icon is selected) may display historical input sections or inputs that have been previously selected. Another (sub-)menu may enable the display of input sections associated with the field of Left Ventricular Hypertrophy. Yet another (sub-) menu may enable the display of input sections associated with the field of Pulmonary Embolism. Yet another (sub-)menu may enable the display of placeholder functions, being input sections comprising placeholder symbols and at least one function (e.g. but no variables).

These listed examples are not exhaustive, and various other types of (sub-) menus would be apparent to the skilled person.

By way of example, interacting with a placeholder symbol may trigger the displaying of at least two interest topics, for selection by the user. Thus, each "interest topic" may represent a menu icon.

The user selecting one or more of the at least two interest topics may trigger the displaying of one or more input sections, for interaction with by the user, wherein the content of the displayed one or more input sections is dependent upon the one or more interest topics selected by the user.

Thus, each interest topic may be provided as a menu icon, selection of which triggers the display of one or more input sections (associated with that interest topic). The input sections may be selected by an operator of the search tool.

An interest topic is a field, concept, (research) area or topic that may be of interest to a user, e.g. "Left Ventricular Hypertrophy" or "Pulmonary Embolism". It may, for example, be a potential research field or interest—i.e. a "research topic".

The interest topics may be dependent upon the database for which the input is to be provided. Thus, if the database is for ECG results/diagnoses, interest topics may include specific sub-fields within this field, such as "Left Ventricular Hypertrophy", "Pulmonary Embolism", "Acute Myocardia Infarction", "Brugada Syndrome" or "Atrial Fibrillation", amongst other possible examples.

Other methods of determining interest topics may be realized, e.g. providing predetermined interest topics only or by processing a user's search history to identify fields or topics in which they are interested. Another method may comprise determining an interest topic based on one or more topics associated with an already selected input section.

A similar approach may be used to define an initialized input. The initialized input may be preset (e.g. comprising a single placeholder, as illustrated in FIG. 1) or may be selected by a user (e.g. based on a list of possible initialized inputs).

For example, an initialized input may be selected by displaying at least two interest topics, for selection by the user, using the visual display system.

Selection by the user of one or more of the interest topics may trigger the displaying of one or more possible visual representations of different initialized inputs, for selection by the user. Each displayed possible visual representation of an input may be dependent upon the one or more interest topics selected by the user.

Selection of one of the displayed possible visual representations of an input may initialize the visual representation of the input based on the selected possible visual representation of the input. Thus, a user may effectively select a "template" for the initialized input.

It is emphasized that this is an optional feature, and, in some embodiments, the initialized input may be preset, e.g. comprise only a single placeholder symbol (as illustrated in FIG. 1).

Figure 5:
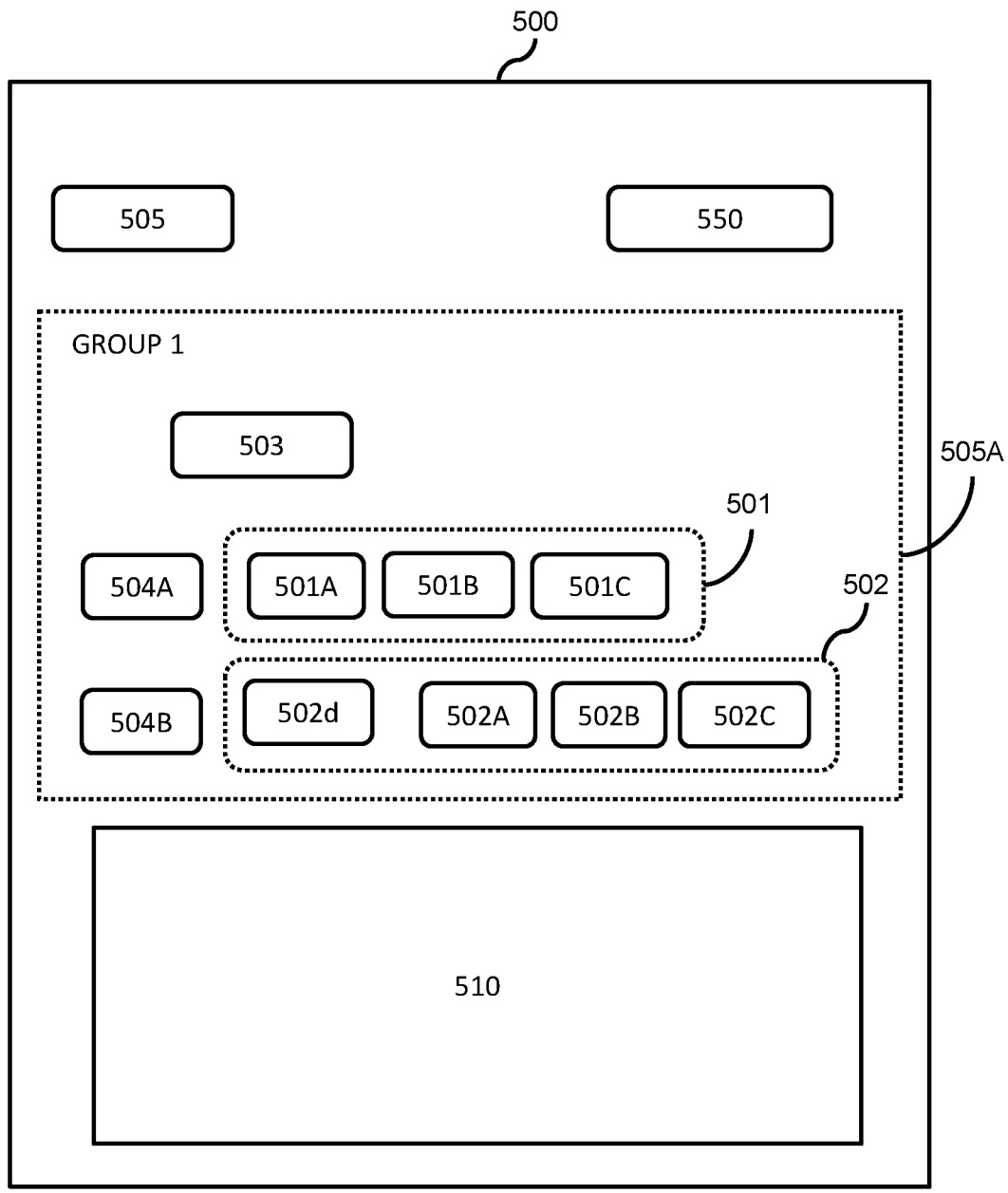
FIG. 5 schematically illustrates a user interface according to an embodiment of the invention.

FIG. 5 illustrates a user interface 500 for a display according to an embodiment of the invention. The user interface 500 enables at least some of the concepts previously described to be implemented.

The user interface 500 comprises various different interactive icons, the operation of which will be made apparent.

The user interface 500 illustrates a scenario in which two different inputs 501, 502 have been created, and are processed to create the overall input for the search engine. Each input is generated by appropriate processing of a respective initialized input using the approach previously described. The skilled person will appreciate that a different number of inputs could be used, i.e. one or more inputs, the number of inputs being defined by a user.

In the illustrated example, each input 501, 502 comprises three elements and defines a search criteria for the search engine. A first input 501 comprises a first variable 501A, a function 501B and a first value 501C. A second input 502 similarly comprises a second variable 502A, a function 502B and a second value 502C. This are only examples, and different inputs may be formatted in a different manner.

A "new input" icon 503 may be selected by a user to create a new initialized input. Selection of the "new input" icon may trigger a process for selecting a new initialized input (e.g. by displaying a plurality of possible interest topics, as previously described) or creation of a new predetermined initialized input (e.g. comprising only a single placeholder symbol, as previously described). In the illustrated scenario, this icon has already been selected twice by a user, to initialize the first 501 and second 502 inputs.

The relationship between the inputs when creating the final input (for the search engine) may also be defined by the user. In the illustrated example, an interactive icon 502d may be used to define the logic used to combine the first and second inputs (e.g. AND or OR logic) to create the overall input. Thus, the interactive icon 502d may be selected by a user to select the logic for combining the inputs.

Interactive deletion icons 504A, 504B may be used to delete an input 501, 502. For example, selection of the first deletion icon 504A may delete the first input 501, whereas selection of the second deletion icon 504B may delete the second input 502. Each deletion icon may be automatically generated when a new input is initialized.

As previously described, each input is iteratively processed until no placeholder symbols are left. The display of suitable input sections (e.g. upon a user interacting with a placeholder symbol, or optionally with an input section) for replacing the placeholder symbol (or input section) may take place in a dedicated area 510 of the user interface.

A search icon 550 may be provided. Selection of the search icon 550 may trigger the generation and/or execution of a search query for a database based on the overall input provided by the user interface (i.e. the combination of the processed inputs 501, 502). Executing the search may comprise returning one or more results of a search, as is known in the art. In some embodiments, the search icon cannot be selected by a user, e.g. may be "greyed out", until there are no placeholder symbols remaining within the overall input. This advantageously prevents an incomplete input from being processed.

For improved ease of organizing the inputs, and improving a user's understanding of the overall input, it may be possible to separate inputs 501, 502 into two or more groups (of inputs). It may be possible to define the relationship between groups of inputs (e.g. whether OR or AND logic is to be used to combine the groups to create the overall input). This may be defined by a user. This approach allows more complex groupings of inputs to be generated. The user interface 500 illustrates a "new group" icon 505 that could be used to create such groups. In the illustrated example, only a single group 505A has been created—"GROUP 1".

In any previously described embodiments, reference to "displaying" takes place by controlling a visual representation provided by an interactive visual display system. The interactive visual display system is adapted to enable a user to interact with an input or placeholder symbols. Suitable interactive visual display systems comprise, for example, a computer, a laptop, a mobile/cellular smartphone, a tablet, a smartwatch and so on.

It has previously been described how a user may be able to interact with different displayed elements. Methods of enabling a user to interact with a displayed element are well known in the prior art and may include, for example, receiving an input from a mouse, a keyboard or a touch-sensitive user interface.

FIG. 5 illustrates a full user interface for a screen. FIGS. 6 to 10 illustrate a number of different steps that could be performed by a user interacting with the screen via such an interface. In these Figures, only the relevant aspects of the user interface for a particular process or step will be illustrated at the relevant point in time, for the purposes of improved conceptual understanding and conciseness. The same reference numerals shall be used where appropriate.

FIGS. 6 to 9 demonstrate a particular sequence of processes or events performed by the user to build up or modify an overall input for the search engine.

Figure 6:
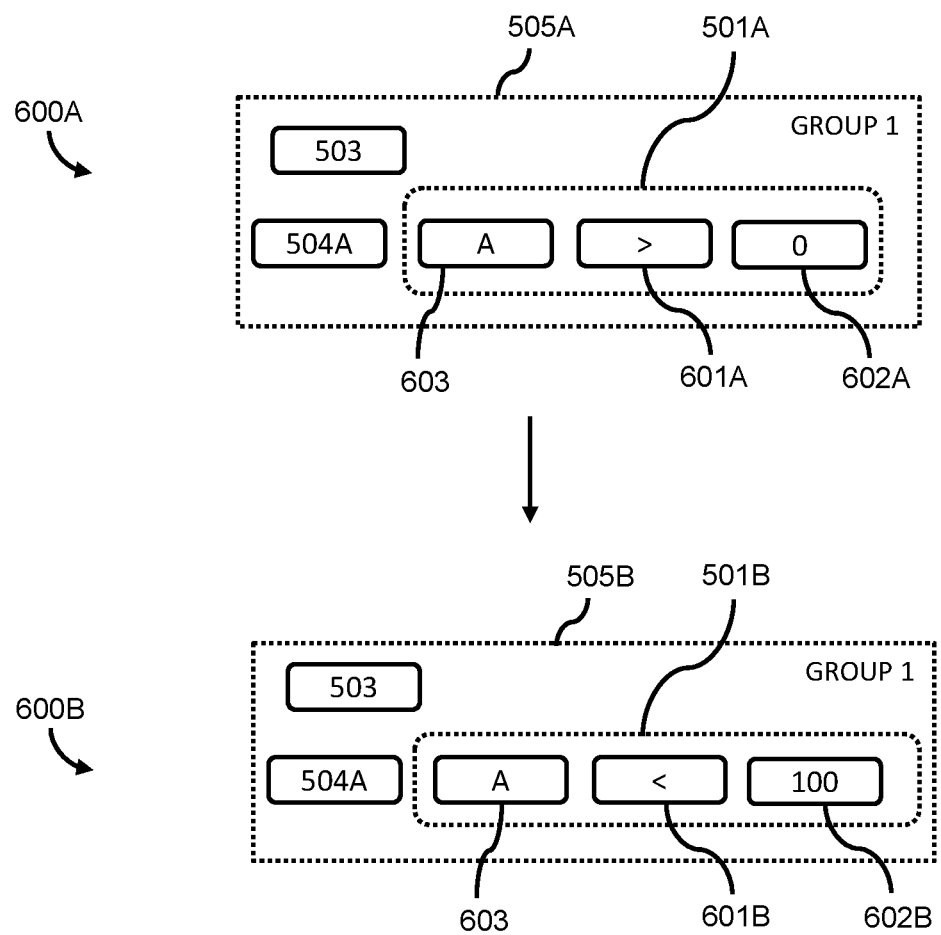
FIGS. 6 to 9 schematically illustrate processes for the user interface according to an embodiment of the invention.

FIG. 6 illustrates a process of replacing a function 601A and a value 602A of a first input 501A with a new function 601B and value 602B, to thereby modify the first input 501A.

At a first point in time 600A, the first input 501A input is formed of a placeholder symbol "A" 603, a function 601A and a value 602A. Example selections ("A", ">" and "0") are shown in each element of the first input 501A for improved understanding. In this scenario, the user wishes to modify the function 601A and the value 602A.

To do so, the user may interact with the function 601A to replace it with a new function 601B. This may be performed, for example, by a drop-down list indicating different possible input sections providing options for the function, or by a separate part of the user interface displaying a list of possible input sections providing options for the function (such as the dedicated area 510 of FIG. 5). The displayed options for the function may depend upon the context of surrounding placeholder symbols, variables and/or variables. By way of example, if the function is disposed between a placeholder/variable and a value, the offered functions may comprise only comparative functions (e.g. ">", "<", "=" and so on).

To modify the value 602A, the user interface may permit the user to input a new desired value (e.g. manually, to replace the value "0" with the value "100"). This increases a level of control of the user over the desired value.

In this way, the original input 501A is modified to create a new input 501B at a second point in time 600B. The placeholder symbol "A" remains unmodified for the time being.

Figure 7:
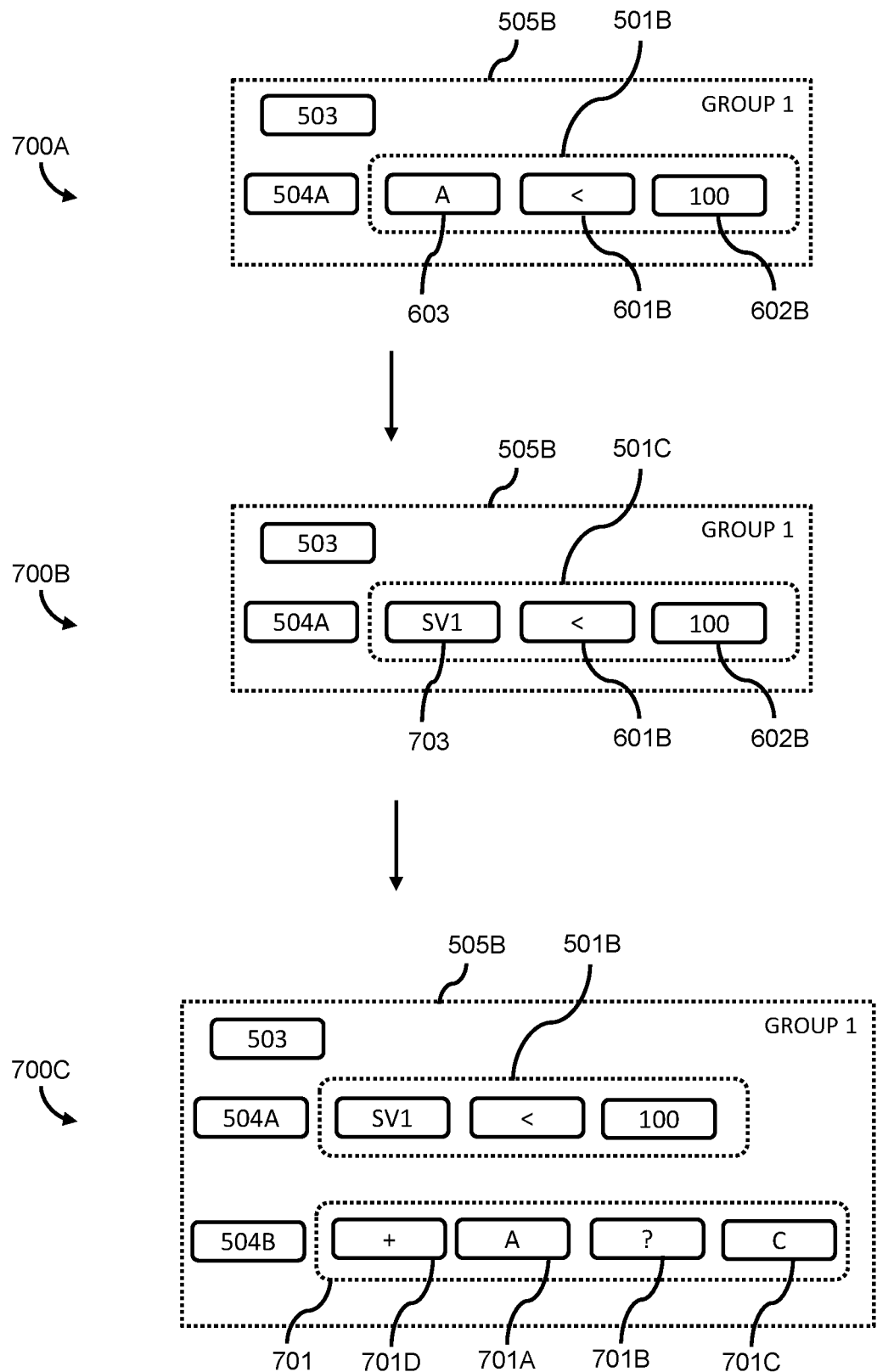

FIG. 7 illustrates a couple of processes that may be performed by the user interacting with the user interface.

A first process, illustrated from a first point in time 700A to a second point in time 700B comprises replacing the placeholder symbol 603 with a variable 703. This may be performed by the user interacting with the placeholder symbol 603, and selecting one of a plurality of input sections each providing a different possible variable for selection.

A second process, illustrated from the second point in time 700B to a third point in time 700C, comprises adding a second input 701 for creating the overall input. Creation of the second input may be performed by the user interacting with the "new input" icon 503, e.g. clicking the "new input" icon 503. Methods of initializing an input have previously been described, e.g. by a user interacting with a list of suitable initialized inputs. Here, the initialized second input 701 comprises a first placeholder "A" 701A, a second placeholder "?" 702B and a third placeholder "C" 702C. An interactive icon 701D may be used to define the logic used to combine the first and second inputs (e.g. AND or OR logic) to create the overall input.

Figure 8:
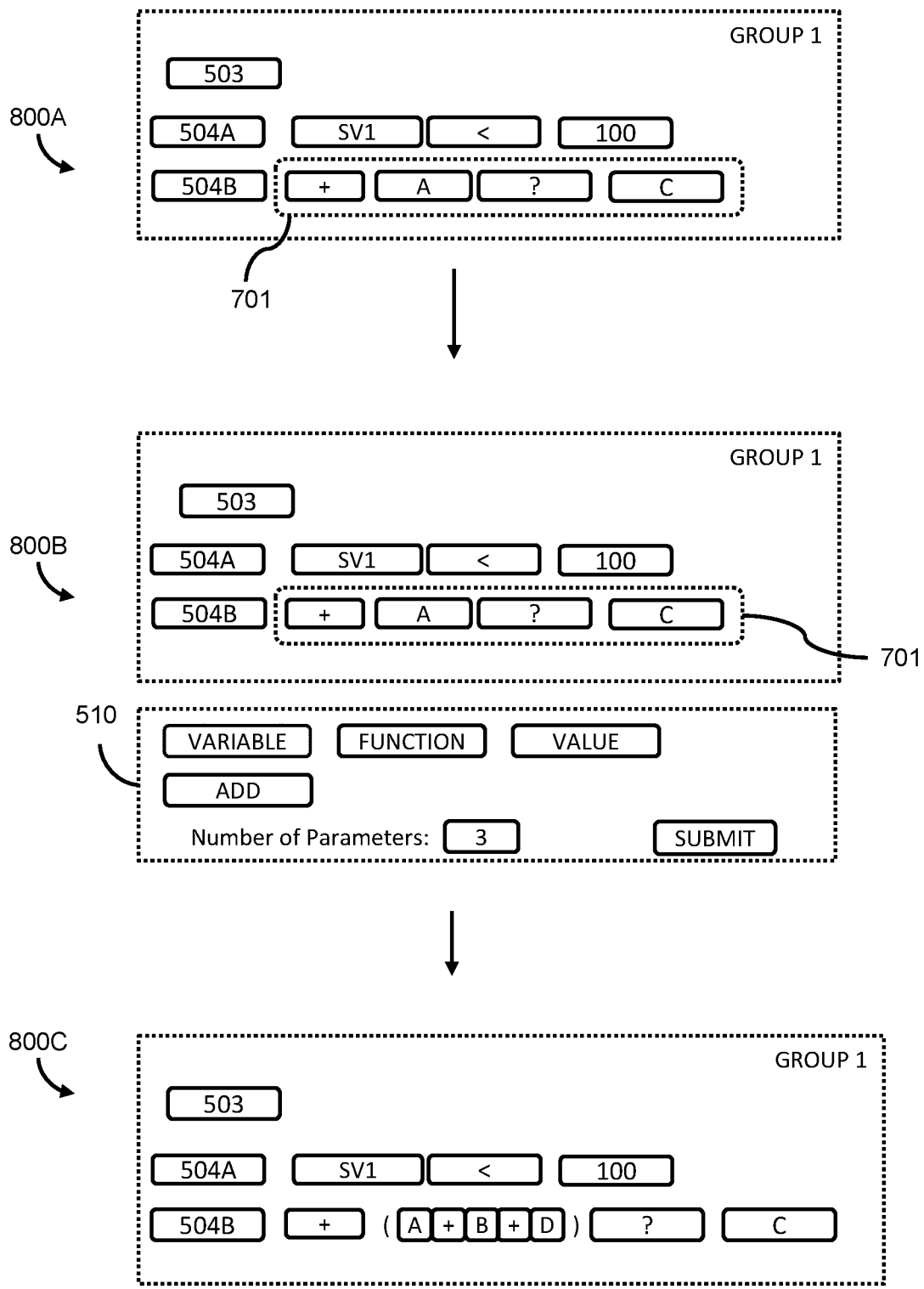

FIG. 8 illustrates a further process that may be performed on an initialized input by the user interacting with the user interface. This process takes place from a first point in time 800A to a third point in time 800C.

The process illustrated by FIG. 8 is that of replacing a placeholder symbol of the second input 701 with a plurality of placeholder symbols and one or more functions that link the placeholder symbols together.

At a first point in time 800A, the user interacts with a placeholder symbol "A" of the second input 701, which causes a one or more menu options to be presented to the user (e.g. in a dedicated portion 510 of the user interface).

In the illustrated example, the user is provided with the option of interacting with an icon "VARIABLE" (which triggers the display a list of optional variables (as input sections) for replacing the placeholder symbol), an icon "FUNCTION" (which triggers the display of a list of possible functions (e.g. "ADD" or "MAX") and enable a user to suggest a number of placeholder symbols for the function) or an icon "VALUE" (which causes the placeholder symbols to be replaced with a default, editable value (e.g. 0)).

At a second point in time 800B, the user can then interact with the menu options to select how the placeholder symbol "A" is to be replaced. In this example, the user then interacts with the icon "FUNCTION", thereby indicating that user wishes the placeholder symbol "A" to be replaced with at least a function.

The user then defines the format of the function, in the illustrated example by selecting the option of an "ADD" function, by interacting with a further menu icon (e.g. from a list of possible functions). The user can also defines the number of parameters that will be included within the function (here: defining the number of placeholder symbols for use in the function).

At the third point in time 800C, the selected options for the placeholder symbol "A" replace the placeholder symbol "A". This may be performed in response to the user interacting with a "SUBMIT" icon. In this way, the placeholder symbol "A" is replaced by a plurality of placeholder symbols "A", "B" and "D", together with the function(s) "+" that link the placeholder symbols.

Each placeholder symbol "A", "B" or "D" can itself be further replaced (as will be later exemplified). Similarly, each function may also be edited or modified (e.g. as previously explained with reference to FIG. 6).

Figure 9:
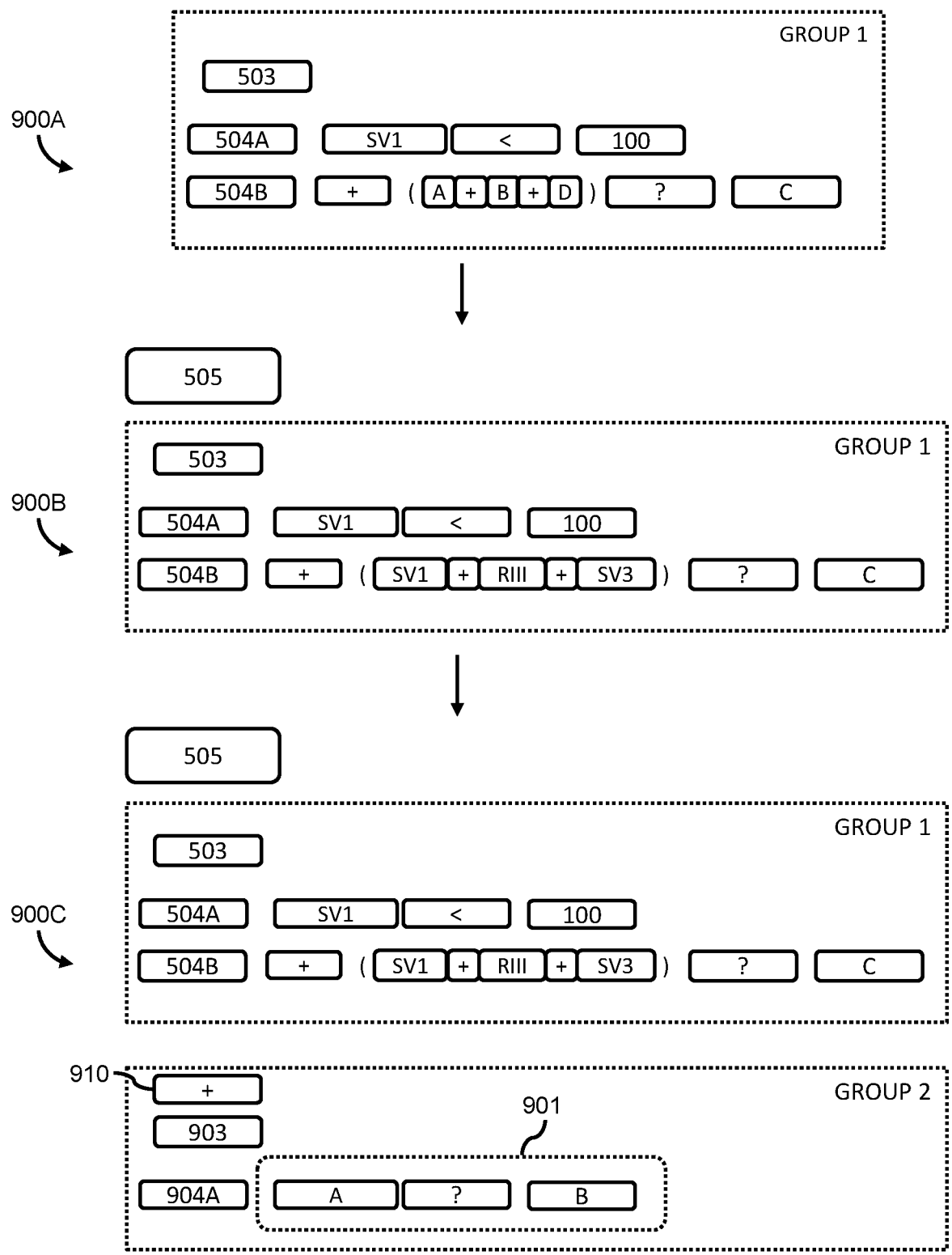

FIG. 9 illustrates some further processes that can be performed using the user interface.

At a first point in time 900A, the user is able to interact with the placeholder symbols "A", "B" and "D" to replace them with variables (here: "SV1", "RIII" and "SV3" respectively). As previously explained, interacting with a placeholder causes a plurality of input sections to be displayed, including one or more variables for selection. The user interacts with a displayed input section to select the variable to replace the placeholder, as previously explained.

The second point in time 900B illustrates the replaced placeholders.

The user is also able to interact with the user interface to create a new group "GROUP 2". This is performed by the user interacting with the "new group" icon 505. For the avoidance of doubt, this icon has been continually present in the user interface (see FIG. 5), but has not been previously illustrated in FIGS. 7 to 8 for the sake of providing concise image.

Selection of the "new group" icon 505 creates a new group, the new group enabling a user to create yet further inputs, such as the initialized input 901 (which here comprises three placeholder symbols). Of course, the new group may comprise a "new input" icon 903 and a delete input icon 904A, which may operate according to previously described methods.

The new group is illustrated as being present at a third point in time 900C.

The user may be able to control how the groups of inputs are combined (e.g. whether OR or AND logic is used) to create the overall input by interacting with a group combination icon 910.

The illustrated steps performed by the user interface are only exemplary and non-exhaustive, any may be omitted in some embodiments.

It has been previously described how the proposed concept of generating an input for a search engine is particularly useful for searching ECG-based databases. A brief description of preparing an ECG database is hereafter provided for improved understanding.

An entry for an ECG database is generated by collecting one or more raw ECG waveforms (measured from a patient). Each waveform may be obtained from a different lead, as is known in the art. An entry can be generated by extracting some information from the ECG waveform(s). This is performed using one or more algorithms, e.g. a machine-learning method, a pattern recognition algorithm or a signal processing method, and/or from user input (e.g. a user analyzing the waveform(s)). The extracted information may comprise, for example, known ECG measurements or diagnosis statements, which may be provided as statement codes (e.g. ABMI, AAPMI and so on). The raw waveform(s) and extracted information form an entry in the database.

The skilled person would appreciate that there are numerous different possible ECG measurements, which may be based upon the duration, amplitude, area, or shape of part of one or more waveforms. Some measurements are based on a combination of all/some of the waveforms.

This process can be repeated for numerous different patients and/or subjects, each forming their own entry in the database.

The ECG database can then be searched based on the variables and/or values of the entries (e.g. of the ECG measurements). For example, the database could be searched to find entries for which the average magnitude of one waveform is greater than a certain number. The input for the search is generated using a previously described method.

Figure 10:
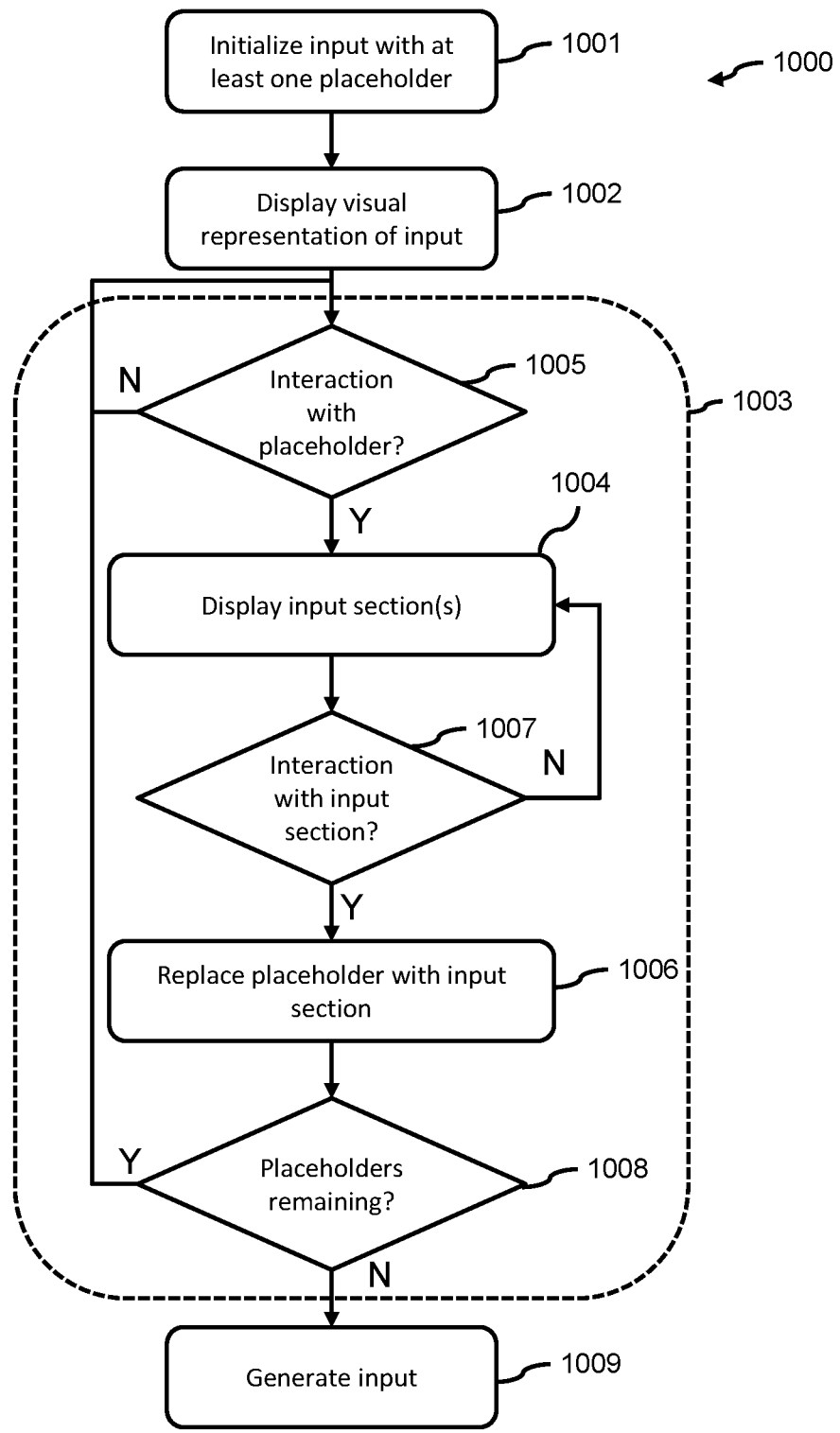
FIG. 10 illustrates a computer-implemented method according to an embodiment of the invention.

Although concepts of the invention have been previously described in general terms, FIG. 10 explicitly illustrates a method 1000 of generating an input for a search engine according to an embodiment of the invention. The method may be for generating an input for a search engine for searching a database storing one or more entries of electrocardiography, ECG, information of one or more patients, The skilled person would be capable of adapting the proposed method to be capable of performing any previously described concept.

The method 1000 comprises a step 1001 of initializing a visual representation of an input for the search engine, the initialized visual representation of the input comprising at least one interactive placeholder symbol;

The method 1000 also comprises a step 1002 of displaying the visual representation of the input using an interactive visual display system.

The method 1000 also comprises an iterative replacement process 1003 that is performed until the input no longer comprises any placeholder symbols.

The iterative replacement process comprises a step of in response to a user interacting with a placeholder symbol, displaying 1004 one or more input sections, for interaction with by the user, using the visual display system.

This step may be achieved by performing a step 1005 of determining whether the user has interacting with a placeholder symbol, and in response to a positive determination (i.e. a user has interacted with a placeholder symbol) performing step 1004, otherwise repeating step 1005.

After performing step 1004, the iterative process 1003 comprises in response to a user interacting with a displayed input section, replacing 1006 the placeholder symbol with the displayed input section.

This step may be achieved by performing a step 1007 of determining whether the user has interacted with a displayed input section, and in response to a positive determination (i.e. the user has interacted with the displayed input section), performing step 1006, otherwise repeating step 1007.

As previously noted, the iterative process 1003 is performed until the input no longer comprises any placeholder symbols. This can be achieved by performing a step 1008 of determining whether there are any placeholder symbols left, and in response to a positive determination (i.e. there is at least one placeholder symbol left), repeating the iterative process, otherwise, the iterative process ends.

After the iterative process 1003 ends, a step 1009 is performed. Step 1009 comprises generating the input for the search engine using the visual representation of the input. Of course, as previously described, step 1009 may comprise using more than one input (which has undergone the iterative process) to generate the input for the search engine ("the overall input").

It will be clear that each of the one or more input sections comprises one or more interactive placeholder symbols and/or one or more variables/values for an input for a search engine.

Figure 11:
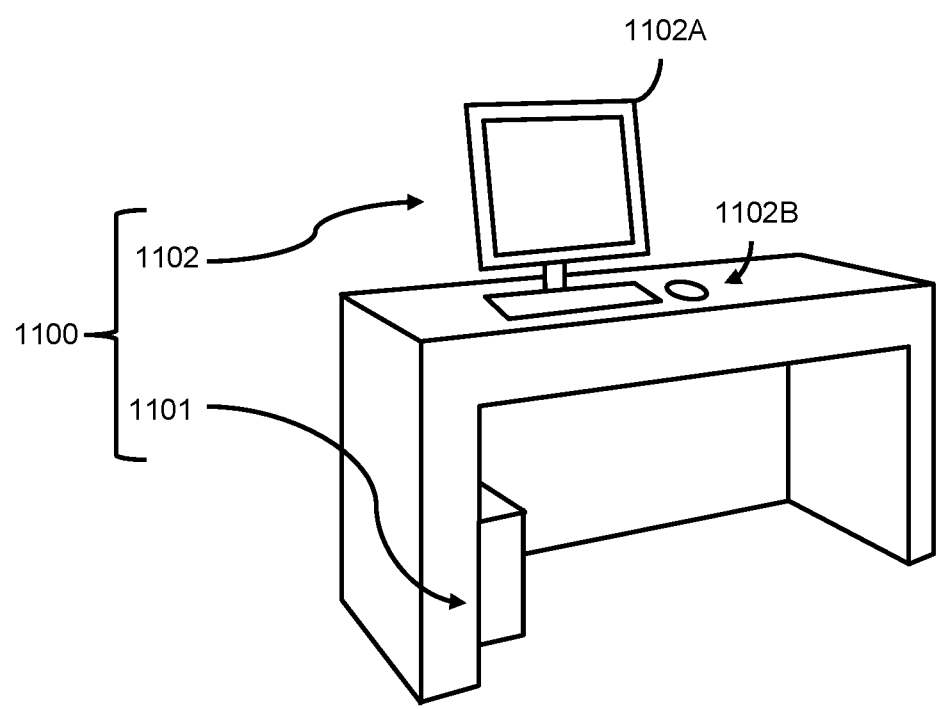
FIG. 11 illustrates an input interface system according to an embodiment of the invention.

FIG. 11 illustrates an input interface system 1100 for generating an input for a search engine, which may be for searching a database storing one or more entries of electrocardiography, ECG, information of one or more patients.

The input interface system comprises a processing system 1101 and an interactive visual display 1102 adapted to enable a user to interact with elements displayed by the visual display.

The processing system 1101 is adapted to perform any previously described method. The processing system may be adapted to carry out any herein described concept, e.g. as described with reference to FIGS. 1 to 6.

Thus, the processing system 1101 is adapted to initialize a visual representation of an input for the search engine, the initialized visual representation of the input comprising at least one interactive placeholder symbol; display the visual representation of the input using an interactive visual display system; and iteratively perform a replacement process until the visual representation of the input no longer comprises any placeholder symbols, the replacement process comprising steps of: in response to a user interacting with a placeholder symbol, displaying one or more input sections, for interaction with by the user, using the visual display system; and in response to a user interacting with a displayed input section, replacing the placeholder symbol with the displayed input section; and generate the input for the search engine using the visual representation of the input, wherein each of the one or more input sections comprises one or more interactive placeholder symbols and/or one or more variables for an input for a search engine.

The interactive visual display 1102 may comprise a display screen 1102A (for providing the visual representations) and one or more input modules 1102B (e.g. a mouse or keyboard) to enable a user to interact with displayed elements. Of course, the display screen may itself form an input module, e.g. be touch-sensitive.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or 70 more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method of generating an input for a search engine for searching at least a database storing one or more entries of electrocardiography (ECG) information of one or more patients, each entry of the database comprises at least one ECG waveform of a patient and one or more of: a value for a parameter derivable from the at least one ECG waveform and a value for a parameter of the patient associated with the at least one ECG waveform, the method comprising:
    initializing a visual representation of an input for the search engine, the initialized visual representation of the input comprising at least one interactive placeholder symbol;
    displaying the visual representation of the input using an interactive visual display system; and
    iteratively performing a replacement process until the visual representation of the input no longer comprises any placeholder symbols, the replacement process comprising steps of:
        in response to a user interacting with a placeholder symbol, displaying one or more input sections, for interaction with by the user, using the visual display system; and
        in response to a user interacting with a displayed input section, replacing the placeholder symbol with the displayed input section; and
    generating the input for the search engine using the visual representation of the input,
    wherein each of the one or more input sections comprises at least one of: an interactive placeholder symbol, a variable for an input for the search engine comprising an identifier of a parameter derivable from at least one ECG waveform of a patient or an identifier of a parameter of the patient associated with the at least one ECG waveform, and/or a value for the variable.

2. The computer-implemented method of claim 1, wherein at least one of the one or more input sections comprises one or more interactive placeholder symbols.

3. The computer-implemented method of claim 2, wherein each input section that comprises one or more interactive placeholder symbols comprises at least one function and at least one interactive placeholder symbol.

4. The computer-implemented method of claim 1, wherein at least one input section comprises at least one function and at least two interactive placeholder symbols.

5. The computer-implemented method of claim 1, wherein the step of initializing a visual representation of an input for the search engine comprises:
    displaying at least two interest topics, for selection by the user, using the visual display system;
    in response to a user selecting one or more of the interest topics, displaying one or more possible visual representations of an input, for selection by the user, using the visual display system, each displayed possible visual representation of an input being dependent upon the one or more interest topics selected by the user; and
    in response to a user selecting a possible visual representation of an input, initializing the visual representation of the input based on the selected possible visual representation of the input.

6. The computer-implemented method of claim 1, wherein in the step of generating the input for the search engine comprises generating a query script for searching a database using the visual representation of the input.

7. The computer-implemented method of claim 1, wherein the step of displaying one or more input sections comprises:
    displaying a first menu icon and a second menu icon to the user, using the visual display system;
    in response to the user interacting with the first menu icon, displaying a first set of one or more input sections to the user, using the visual display system, each input section in the first set comprising one or more variables for an input for a search engine;
    in response to the user interacting with the second menu icon, displaying a second set of one or more input sections to the user, using the visual display system, each input section in the second set comprising one or more selectable placeholder symbols.

8. The computer-implemented method of claim 1, wherein the step of displaying one or more input sections during the replacement process comprises:
    displaying at least two interest topics, for selection by the user, using the visual display system;
    in response to a user selecting one or more of the at least two interest topics, displaying one or more input sections, for interaction with by the user, using the visual display system, wherein the displayed one or more input sections are dependent upon the one or more interest topics selected by the user.

9. The computer-implemented method of claim 1, further comprising performing a search using the generated input for the search engine.

10. A computer program comprising code means for implementing the computer-implemented method of claim 1 when said program is run on a processing system.

11. A processing system adapted to generate an input for a search engine for searching at least a database storing one or more entries of electrocardiography (ECG) information of one or more patients, each entry of the database comprises at least one ECG waveform of a patient and one or more of: a value for a parameter derivable from the at least one ECG waveform and a value for a parameter of the patient associated with the at least one ECG waveform, the processing system being adapted to:
    initialize a visual representation of an input for the search engine, the initialized visual representation of the input comprising at least one interactive placeholder symbol;
    display the visual representation of the input using an interactive visual display system; and iteratively perform a replacement process until the visual representation of the input no longer comprises any placeholder symbols, the replacement process comprising steps of:

in response to a user interacting with a placeholder symbol, displaying one or more input sections, for interaction with by the user, using the visual display system; and in response to a user interacting with a displayed input section, replacing the placeholder symbol with the displayed input section; and generate the input for the search engine using the visual representation of the input, wherein each of the one or more input sections comprises at least one of: an interactive placeholder symbol, a variable for an input for a search engine comprising an identifier of a parameter derivable from at least one ECG waveform of a patient or an identifier of a parameter of the patient associated with the at least one ECG waveform, and/or a value for a variable.

12. The processing system of claim 11, wherein at least one of the one or more input sections comprises one or more selectable placeholder symbols.

13. The processing system of claim 11, wherein at least one input section comprises at least one function and at least two interactive placeholder symbols.

14. An input interface system for generating an input for a search engine, the input interface system comprising:

the processing system of claim 11; and an interactive visual display adapted to enable a user to interact with elements displayed by the visual display.

* * * * *